United States Patent
Taguchi et al.

(10) Patent No.: US 9,747,704 B2
(45) Date of Patent: Aug. 29, 2017

(54) X-RAY COMPUTED TOMOGRAPHY APPARATUS AND MEDICAL IMAGE PROCESSING APPARATUS

(71) Applicant: Toshiba Medical Systems Corporation, Otawara-shi (JP)

(72) Inventors: Hiroki Taguchi, Otawara (JP); Satoru Nakanishi, Arlington Heights, IL (US)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/789,243

(22) Filed: Jul. 1, 2015

(65) Prior Publication Data

US 2015/0348292 A1 Dec. 3, 2015

Related U.S. Application Data

(63) Continuation of application No. PCT/JP2014/050086, filed on Jan. 7, 2014.

(30) Foreign Application Priority Data

Jan. 7, 2013 (JP) ................................. 2013-000695
Jan. 7, 2014 (JP) ................................. 2014-001145

(51) Int. Cl.
*G06K 9/00* (2006.01)
*A61B 6/00* (2006.01)
(Continued)

(52) U.S. Cl.
CPC .............. *G06T 11/005* (2013.01); *A61B 6/03* (2013.01); *A61B 6/032* (2013.01); *A61B 6/482* (2013.01);
(Continued)

(58) Field of Classification Search
USPC ........ 382/100, 103, 106–107, 128–133, 154, 382/162, 168, 181, 191, 209, 219, 224,
(Continued)

(56) References Cited

U.S. PATENT DOCUMENTS

2009/0129539 A1 5/2009 Licato et al.
2009/0147919 A1* 6/2009 Goto ...................... A61B 6/032
378/86

(Continued)

FOREIGN PATENT DOCUMENTS

JP 2007-44275 A 2/2007
JP 2009-125584 A 6/2009
(Continued)

OTHER PUBLICATIONS

International Search Report issued Feb. 10, 2014 for PCT/JP2014/050086 filed on Jan. 7, 2014 with English Translation.

(Continued)

*Primary Examiner* — Seyed Azarian
(74) *Attorney, Agent, or Firm* — Oblon, McClelland, Maier & Neustadt, L.L.P.

(57) ABSTRACT

An X-ray computed tomography apparatus according to embodiments includes image processing circuitry and decomposition circuitry. The image processing circuitry is configured to perform an image processing on each of a plurality of pieces of monochromatic X-ray image data of different energies, the plurality of pieces of monochromatic X-ray image data being generated from projection data. The decomposition circuitry is configured to decompose, for each of a plurality of basis materials specified in advance, the plurality of pieces of monochromatic X-ray image data after the image processing, to generate basis material image data of each of the plurality of basis materials.

10 Claims, 5 Drawing Sheets

(51) Int. Cl.
  *G06T 11/00* (2006.01)
  *A61B 6/03* (2006.01)
  *G06T 7/00* (2017.01)

(52) U.S. Cl.
  CPC .......... *A61B 6/5205* (2013.01); *G06T 7/0012* (2013.01); *G06T 2207/10081* (2013.01); *G06T 2207/10116* (2013.01); *G06T 2207/30004* (2013.01); *G06T 2211/40* (2013.01)

(58) Field of Classification Search
  USPC ....... 382/232, 254, 274–276, 287, 291, 294, 382/305, 312; 378/4, 5, 21, 16, 86
  See application file for complete search history.

(56) References Cited

U.S. PATENT DOCUMENTS

2009/0262997 A1* 10/2009 Zou ...................... G06T 11/005
                                                                 382/131
2010/0189212 A1*  7/2010 Zou ...................... G06T 11/005
                                                                 378/5
2012/0039440 A1   2/2012 Fan et al.
2012/0236984 A1*  9/2012 Chandra ................ A61B 6/032
                                                                 378/16
2014/0363069 A1* 12/2014 Hsieh ...................... G06T 5/005
                                                                 382/131

FOREIGN PATENT DOCUMENTS

| JP | 2009-261942 A | 11/2009 |
| JP | 2010-082031 A |  4/2010 |
| JP | 2011-244875 A | 12/2011 |
| JP | 2012-245235 A | 12/2012 |

OTHER PUBLICATIONS

Written Opinion issued Feb. 10, 2014 for PCT/JP2014/050086 filed on Jan. 7, 2014.

* cited by examiner

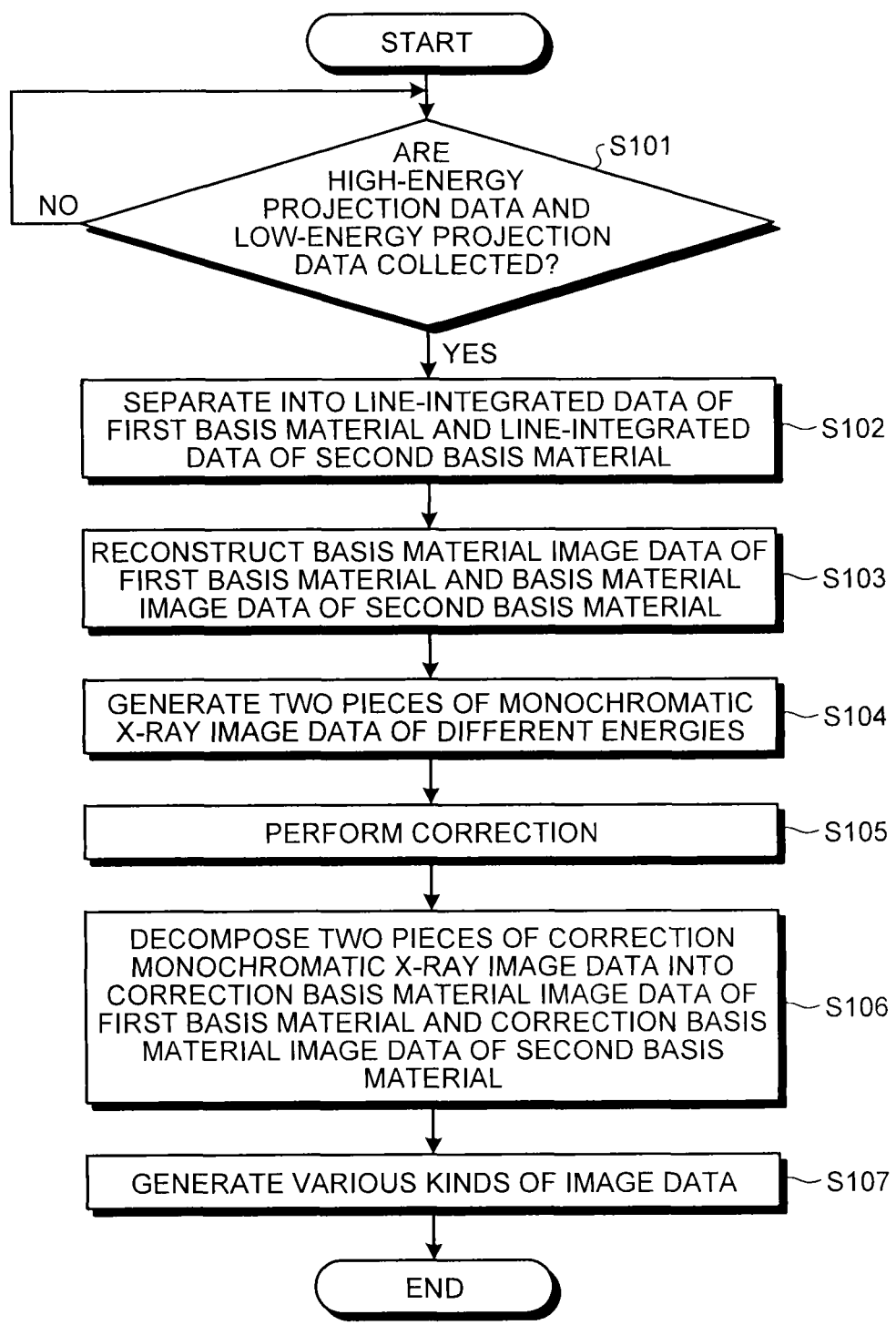

X-RAY COMPUTED TOMOGRAPHY APPARATUS AND MEDICAL IMAGE PROCESSING APPARATUS

CROSS-REFERENCE TO RELATED APPLICATIONS

This application is a continuation of PCT international application Ser. No. PCT/JP2014/050086 filed on Jan. 7, 2014 which designates the United States, the entire contents of which are incorporated herein by reference, and which claims the benefit of priority from Japanese Patent Application No. 2013-000695, filed on Jan. 7, 2013, and Japanese Patent Application No. 2014-001145, filed on Jan. 7, 2014; the entire contents of which are incorporated herein by reference

FIELD

Embodiments described herein relate generally to an X-ray computed tomography and a medical image processing apparatus.

BACKGROUND

Conventionally, a method of acquiring images by performing imaging with a plurality of different tube voltages by an X-ray computed tomography (CT) apparatus is available. The method is called "dual energy CT" when two different tube voltages are used. Moreover, for dual energy CT, an applied technique has been known in which two pieces of projection data collected at two different tube voltages are separated into projection data (line-integrated data) of two basis materials specified in advance, and images (basis material images) based on the abundance ratio of the basis materials are reconstructed from each of the two separated data. In the applied technique, by performing weighting calculation processing using the two basis material images, various kinds of images such as a monochromatic X-ray image, a density image, and an effective atomic number image can be acquired.

However, various kinds of the images acquired by the above applied technology are often not images of CT value information. Therefore, conventional correction processing that has been performed using CT value information after reconstruction of an X-ray CT image is often inapplicable to the various kinds of images that are acquired by the above applied technology. That is, conventionally, there is a case when it is impossible to improve the image quality of various kinds of the images that are acquired by the above applied technology.

BRIEF DESCRIPTION OF THE DRAWINGS

FIG. 7 is a flowchart showing an example of processing performed by the X-ray CT apparatus according the present embodiment.

DETAILED DESCRIPTION

An X-ray computed tomography apparatus according to embodiments includes image processing circuitry and decomposition circuitry. The image processing circuitry is configured to perform an image processing on each of a plurality of pieces of monochromatic X-ray image data of different energies, the plurality of pieces of monochromatic X-ray image data being generated from projection data. The decomposition circuitry is configured to decompose, for each of a plurality of basis materials specified in advance, the plurality of pieces of monochromatic X-ray image data after the image processing, to generate basis material image data of each of the plurality of basis materials.

Embodiments of an X-ray CT apparatus are explained is detail below with reference to the accompanying drawings.

(Embodiment)

Figure 1:
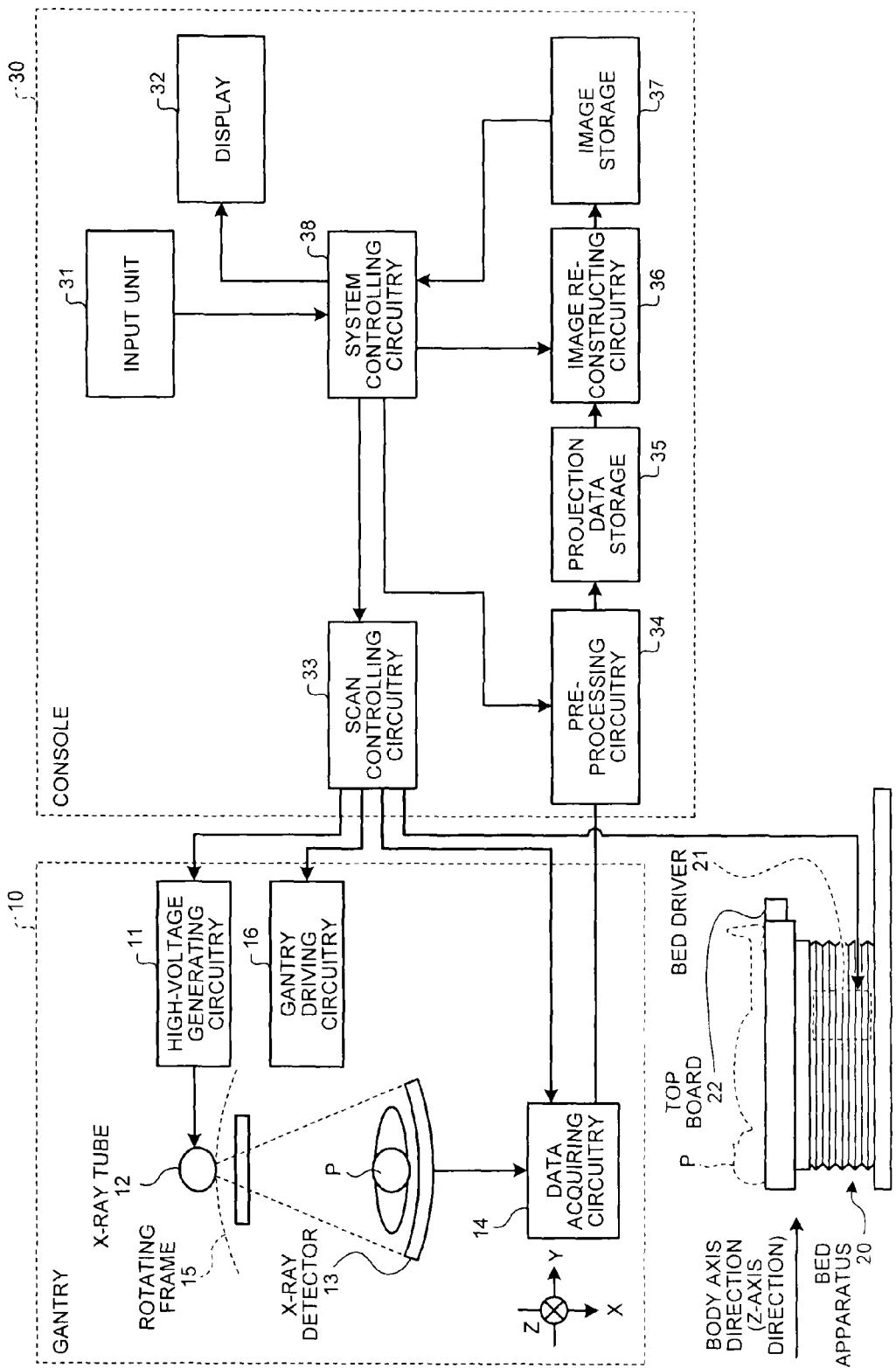
FIG. 1 is a schematic diagram illustrating an example of an entire configuration of an X-ray CT apparatus according to a present embodiment.

First, an example of an entire configuration of an X-ray CT apparatus according to a present embodiment is explained using FIG. 1. FIG. 1 is a schematic diagram illustrating an example of the entire configuration of the X-ray CT apparatus according to the present embodiment. As shown in FIG. 1, the X-ray CT apparatus according to the present embodiment includes a gantry 10, a bed apparatus 20, and a console 30.

The gantry 10 is a device that collects X-ray detection data by applying X-rays to a subject P, and includes high-voltage generating circuitry 11, an X-ray tube 12, an X-ray detector 13, data acquiring circuitry 14, a rotating frame 15, and gantry driving circuitry 16.

The high-voltage generating circuitry 11 is a device that generates a high voltage, and provides the generated high voltage to the X-ray tube 12. The X-ray tube 12 is a vacuum tube that generates X-rays by applying the high voltage provided by the high-voltage generating circuitry 11. The X-rays generated by the X-ray tube 12 is irradiated to the subject P.

The X-ray detector 13 is a detector that detects X-ray detection data indicating an intensity distribution of X-rays that have irradiated from the X-ray tube 12 and passed through the subject P. In other words, the X-ray detector 13 detects the X-ray detection data indicating the degree of X-ray absorption inside the subject P. For example, the X-ray detector 13 is a two-dimensional arrayed detector in which detector element lines in which a plurality of X-ray detector elements is aligned along a direction of channel (Y-axis direction shown in FIG. 1) are arranged along a direction of a body axis of the subject P (Z-axis direction shown in FIG. 1).

The rotating frame 15 supports the X-ray tube 12 and the X-ray detector 13 across the subject P in between. The gantry driving circuitry 16 is a device that rotates the X-ray tube 12 and the X-ray detector 13 along a circular orbit having the subject P in a center by driving the rotating frame 15 to rotate.

The data acquiring circuitry 14 is a data acquisition system (DAS), and collects X-ray detection data that is detected by the X-ray detector 13. Specifically, the data acquiring circuitry 14 collects X-ray detection data that corresponds to each X-ray irradiation direction from the X-ray tube 12. The X-ray irradiation direction is also called view. The data acquisition circuitry 14 performs an amplification processing, an analog-to-digital (A/D) conversion processing, and the like on the acquired X-ray detection data of each view, to output to pre-processing circuitry 34 (described later) in the console 30. For example, the data acquiring circuitry 14 outputs data (sinogram data) in which X-ray detection data indicating the amount of detected X-ray at each X-ray detector element is chronologically arranged for each X-ray irradiation direction.

The bed apparatus 20 is an equipment to mount the subject P, and includes a top board 22 and a bed driver 21 as shown in FIG. 1. The top board 22 is a bed on which the subject P is laid, and the bed driver 21 moves the subject P into the rotating frame 15 by moving the top board 22 in a direction of the body axis (Z-axis direction) of the subject P.

The console 30 is a device that accepts an operation of the X-ray CT apparatus by an operator and reconstructs tomography image data or volume data from a projection data group acquired by the gantry 10, and includes an input unit 31, a display 32, scan controlling circuitry 33, the pre-processor 34, a projection data storage 35, image reconstructing circuitry 36, an image storage 37, and system controlling circuitry 38 as shown in FIG. 1.

The input unit 31 has a mouse, a keyboard, a button, a trackball, a joystick, and the like for an operator such as a doctor and a technician that operates the X-ray CT apparatus to input various kinds of instructions, and transfers various kinds of commands received from the operator to the system controlling circuitry 38 described later.

The display 32 has a monitor to display a graphical user interface (GUI) to accept an instruction from an operator through the input unit 31, and to display an image that is stored in the image storage 37 described later.

The scan controlling circuitry 33 controls operation of the high-voltage generating circuitry 11, the gantry driving circuitry 16, the data acquiring circuitry 14, and the bed driver 21. Thus, the scan controlling circuitry 33 controls an X-ray scan processing on the subject P in the gantry 10, a collection processing of an X-ray detection data group, and a data processing for the X-ray detection data group.

Specifically, the scan controlling circuitry 33 executes X-ray scanning by irradiating X-rays from the X-ray tube 12 consecutively or intermittently while rotating the rotating frame 15. For example, the scan controlling circuitry 33 executes helical scan in which imaging is performed consecutively rotating the rotating frame 15 while moving the top board 22, or conventional scan in which imaging is performed rotating the rotating frame 15 with one full rotation or with continuous rotations while the position of the subject P is fixed.

The pre-processing circuitry 34 generates projection data by performing a logarithm conversion processing and a correction processing, such as an offset correction, a sensitivity correction, and a beam hardening correction, on the X-ray detection data transmitted from the data acquiring circuitry 14. The processing performed by the pre-processing circuitry 34 according to the present embodiment is described in detail later.

The projection data storage 35 stores projection data that is generated by the pre-processing circuitry 34.

The image reconstructing circuitry 36 generates various kinds of images from the projection data stored in the projection data storage 35, and stores the generated images in the image storage 37. For example, the image reconstructing circuitry 36 reconstructs an X-ray CT image by performing a back projection processing (for example, the back projection processing by a filtered back projection (FBP) method), and stores the reconstructed X-ray CT image in the image storage 37. The processing performed by the image reconstructing circuitry 36 according to the present embodiment is described in detail later.

The system controlling circuitry 38 controls the entire X-ray CT apparatus by controlling operation of the gantry 10, the bed apparatus 20, and the console 30. Specifically, the system controlling circuitry 38 controls the scan controlling circuitry 33 to control the collection processing of the X-ray detection data group performed by the gantry 10 and the bed apparatus 20. Moreover, the system controlling circuitry 38 controls the pre-processing circuitry 34 and the image reconstructing circuitry 36 to control the image processing performed in the console 30. Furthermore, the system controlling circuitry 38 performs control to display various kinds of images stored in the image storage 37 on the display 32.

As above, the entire configuration of the X-ray CT apparatus according to the present embodiment has been explained. With the configuration, the X-ray CT apparatus according to the embodiment collects projection data by performing "multi energy imaging" with a plurality of different tube voltages, in addition to a collection of projection data by imaging with a fixed single tube voltage. For example, the X-ray CT apparatus according to the present embodiment collects projection data by performing "dual energy imaging" with two different tube voltages.

The "dual energy imaging" is performed, for example, by following three imaging methods. The first imaging method is the "slow-kilovolt (kV) switching method (double rotation method)". The second imaging method is the "dual source method (two tubes method)" in which imaging is performed with different tube voltages using a two-tubes X-ray CT apparatus, not a one-tube X-ray CT apparatus as shown in FIG. 1. The third imaging method is the "fast-kV switching method (high-speed switching method)" in which imaging is performed switching tube voltages at high speed for each view while rotating the rotating frame 15. By these methods, two types of raw data (projection data) of different energies can be acquired.

In the following, a case in which the "dual energy imaging" is performed by the high-speed switching method is explained. The present embodiment is also applicable when the "dual energy imaging" is performed by the double rotation method or the two tubes method.

Conventionally, X-ray CT images have been reconstructed from each of projection data of high energy and projection data of low energy, and images that are obtained by performing weighted addition of the two reconstructed X-ray CT images at an arbitrary ratio have been generated.

Furthermore, recently, an applied technique of reconstructing an image (basis material image) based on the abundance ratio of the basis materials by separating two pieces of projection data acquired with two different tube voltages into projection data (line-integrated data) of each of two basis materials specified in advance has been developed. In this applied technique, by performing a weighting calculation processing using two basis material images, various kinds of images such as a monochromatic X-ray image, a density image, and an effective atomic number image can be acquired.

However, various kinds of images acquired by the above applied technique are often not images having CT value information. Therefore, the conventional correction process that has been performed using CT value information after reconstruction of an X-ray CT image is often inapplicable to the various kinds of images that are acquired by the above applied technique. In the present embodiment, to improve the quality of images that are acquired by imaging with a plurality of different tube voltages, that is, images not having CT value information, the processing of the pre-processing circuitry 34 and the image reconstructing circuitry 36 explained below is performed.

Figure 2:
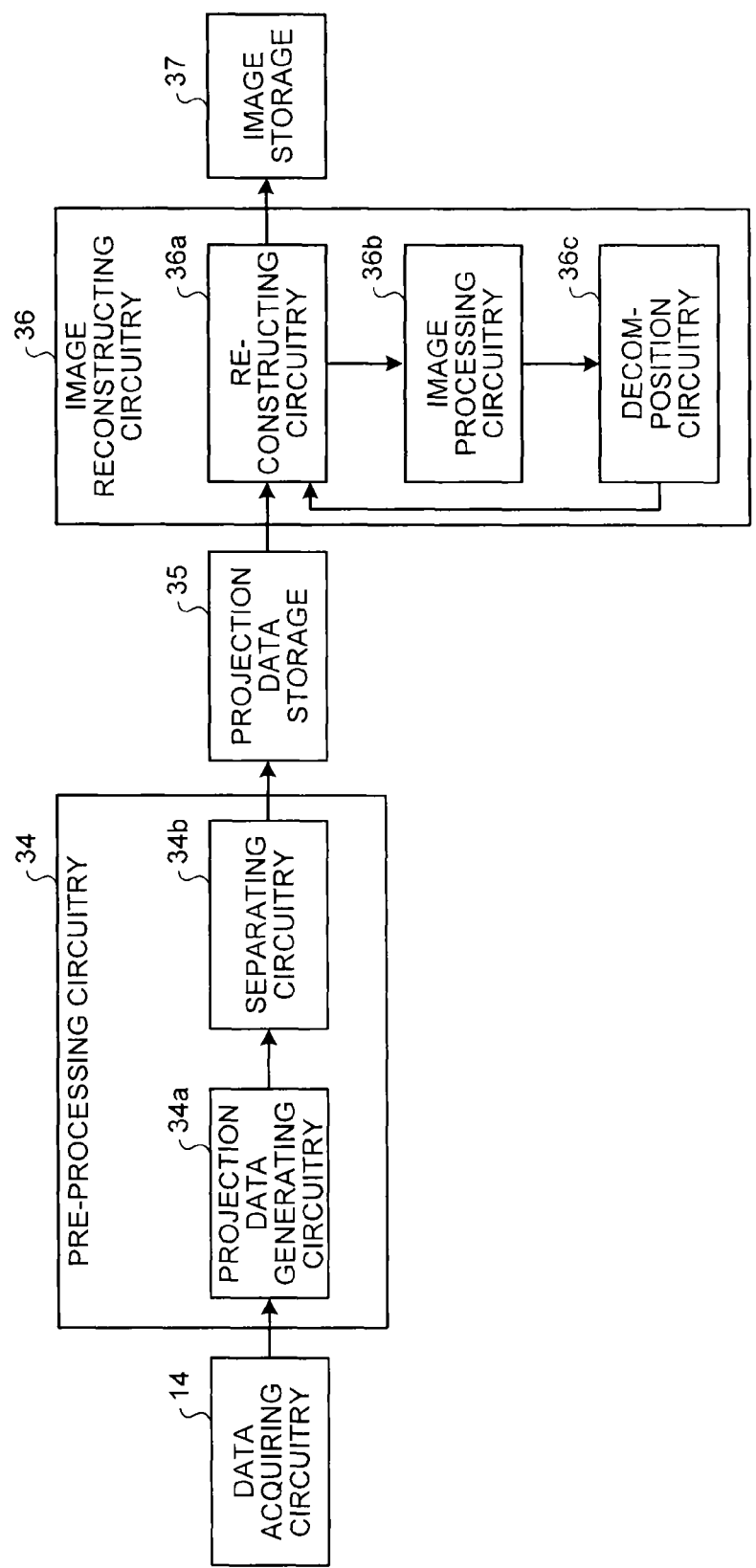
FIG. 2 is a block diagram illustrating a configuration example of pre-processing circuitry and image reconstructing circuitry according to the present embodiment.

FIG. 2 is a block diagram illustrating a configuration example of the pre-processing circuitry and the image reconstructing circuitry according to the present embodiment. As shown in FIG. 2, the pre-processing circuitry 34 according to the present embodiment includes projection data generating circuitry 34a and separating circuitry 34b. Moreover, as shown in FIG. 2, the image reconstructing circuitry 36 includes reconstructing circuitry 36a, image processing circuitry 36b, and decomposition circuitry 36c.

The projection data generating circuitry 34a performs a logarithmic conversion processing and the like on X-ray detection data that is transmitted from the data acquiring circuitry 14, to generate projection data. In the present embodiment, the projection data generating circuitry 34a generates projection data from X-ray detection data of a first tube voltage (for example, 130 kV) (hereinafter, described as high-energy projection data). Furthermore, in the present embodiment, the projection data generating circuitry 34a generates projection data from X-ray detection data of a second tube voltage (for example, 40 kV) (hereinafter, described as low-energy projection data).

The image processing circuitry 36b shown in FIG. 2 performs an image processing on each of a plurality of pieces of monochromatic X-ray image data of different energies, the plurality of pieces of monochromatic X-ray image data being generated from projection data. The decomposition circuitry 36c shown in FIG. 2 decomposes, for each of at least two or more (a plurality of) basis materials specified in advance, the plurality of pieces of monochromatic X-ray image data after the image processing, to generate basis material image data of each of the plurality of basis materials. In the present embodiment, the plurality of pieces of monochromatic X-ray image data described above are generated from projection data by the processing of the separating circuitry 34b and the reconstructing circuitry 36a explained below. The processing of the image processing circuitry 36b and the decomposition circuitry 36c is described in detail later.

The separating circuitry 34b separates the projection data into a plurality of pieces of line-integrated data of each of the two or more (the plurality of) predetermined basis materials. In the present embodiment, the projection data is two pieces of projection data (high-energy projection data and low-energy projection data) collected at two different tube voltages. Furthermore, in the present embodiment, the basis materials described above are two kinds of basis materials, and, for example, bones and water. In the following, one of the two kinds of basis materials is referred to as a first basis material and the other is referred to as a second basis material.

That is, the separating circuitry 34b separates the high-energy projection data and the low-energy projection data into line-integrated data of the first basis material and line-integrated data of the second basis material. The basis material is specified from among materials the attenuation coefficient (linear attenuation coefficient or mass attenuation coefficient) is known at different energy levels.

The processing of the separating circuitry 34b is based on the assumption that the attenuation coefficient of one position in an imaging area at an energy "E" can be expressed by attenuation coefficients of respective two basis materials at the energy "E" and abundance ratios of the respective two basis materials that exist in the position. A line integral of an abundance ratio "$c_1$" of the first basis material and a line integral of an abundance ratio "$c_2$" of the second basis material of a penetrated X-ray "l" are referred to as "first line-integrated data" and "second line-integrated data", respectively. Furthermore, a mean attenuation coefficient of the first basis material and a mean attenuation coefficient of the second basis material at multi-colored high energy are referred to as a "first high-energy mean attenuation coefficient" and a "second high-energy mean attenuation coefficient", respectively. Moreover, a mean attenuation coefficient of the first basis material and a mean attenuation coefficient of the second basis material of multi-colored low energy are referred to as a "first low-energy mean-attenuation coefficient" and a "second low-energy mean-attenuation coefficient", respectively. Furthermore, an error caused by beam hardening at irradiation of a high energy and an error caused by beam hardening at irradiation of a low energy of the penetrated X-ray "l" are referred to as a "high energy error" and a "low energy error", respectively.

The separating circuitry 34b approximates high-energy projection data with an equation using the "first high-energy mean-attenuation coefficient", the "first line-integrated data", the "second high-energy mean-attenuation coefficient", the "second line-integrated data", and the "high energy error". Moreover, the separating circuitry 34b approximates low-energy projection data with an equation using the "first low-energy mean-attenuation coefficient", the "first line-integrated data", the "second low-energy mean-attenuation coefficient", the "second line-integrated data", and the "low energy error". The separating circuitry 34b acquires the first line-integrated data and the second line-integrated data by iteratively solving two approximate expressions. The processing of the separating circuitry 34b is described in Japanese Laid-open Patent Publication No. 2009-261942 and the like, and therefore, detailed explanation is omitted.

The first line-integrated data and the second line-integrated data separated by the separating circuitry 34b are stored in the projection data storage 35.

The reconstructing circuitry 36a reconstructs, from each of the plurality of pieces of line-integrated data of each of the plurality of basis materials, basis material image data in which a pixel value of each pixel (or voxel) indicates an abundance ratio of a basis material that exists in the pixel. The basis material image data that the reconstructing circuitry 36a reconstructs is basis material image data before the image processing performed by the image processing circuitry 36b described later. Furthermore, basis material image data that is generated by the decomposition circuitry 36c is basis material image data after the image processing performed by the image processing circuitry 36b, and is image data that is the basis material image data to which a result of the image processing is reflected.

Specifically, the reconstructing circuitry 36a reconstructs basis material image data of the first basis material by performing the back projection processing on the first line-integrated data. Moreover, the reconstructing circuitry 36a reconstructs basis material image data of the second basis material by performing the back projection processing on the second line-integrated data. In the following, the basis material image data of the first basis material may be described as first basis material image data. Furthermore, in the following, the basis material image data of the second basis material may be described as second basis material image data.

The pixel value of a pixel "i" of the first basis material image data is the abundance ratio "$c_1$" of the first basis material. Moreover, the pixel value of the pixel "i" of the second basis material image data is the abundance ratio "$c_2$" of the second basis material.

The reconstructing circuitry 36a generates the plurality of pieces of monochromatic X-ray image data with different energies, using the reconstructed basis material image data of each of the plurality of basis materials. Specifically, the reconstructing circuitry 36a according to the present embodiment generates monochromatic X-ray image data with each of the same number of different energies as the number of basis materials specified as the plurality of basis materials. That is, in the present embodiment, number of the pieces of the plurality of monochromatic X-ray image data is equal to number of basis materials specified as the plurality of basis materials. In the present embodiment, the number of basis materials is two, that is the first basis material and the second basis material, and accordingly, the reconstructing circuitry 36a generates two pieces of monochromatic X-ray image data at two different energies, using the first basis material image data and the second basis material image data.

A method of generating monochromatic X-ray image data using basis material image data is explained below. For example, let coordinates indicating a position of the pixel "i" on image data be "x" and "y". The pixel value (the abundance ratio of the first basis material) of the first basis material image data at the pixel "x, y" is "$c_1(x, y)$", and the pixel value (the abundance ratio of the second basis material) of the second basis material image data at the pixel "x, y" is "$c_2(x, y)$" Furthermore, the linear attenuation coefficient of the first basis material at the arbitrary energy "E" is "$\mu_1(E)$". Moreover, the linear attenuation coefficient of the second basis material at the arbitrary energy "E" is "$\mu_2(E)$". In this case, a linear attenuation coefficient "$\mu(E, x, y)$" of an imaging part that corresponds to the pixel "x, y" at the energy "E" can be obtained by the following Equation (1) using two pieces of the basis material image data.

$$\mu(E,x,y)=\mu_1(E)c_1(x,y)+\mu_2(E)c_2(x,y) \qquad (1)$$

Moreover, a CT value "CT#(E, x, y)" of the imaging part that corresponds to the pixel "x, y" of "E" is obtained by substituting "$\mu(E, x, y)$" that is obtained by Equation (1) and a linear attenuation coefficient "$\mu_{water}(E)$" of water at "E" into following Equation (2).

$$CT\#(E, x, y) = 1000 \times \frac{\mu(E, x, y) - \mu_{water}(E)}{\mu_{water}(E)} \qquad (2)$$

The reconstructing circuitry 36a can generate monochromatic X-ray image data of the arbitrary energy "E" using the basis material image data and Equation (1) and Equation (2). That is, if two pieces of basis material image data are acquired, a linear attenuation coefficient of an arbitrary energy can be acquired by Equation (1), and by substituting this linear attenuation coefficient into Equation (2), a CT value can be acquired. The reconstructing circuitry 36a generates monochromatic X-ray image data by performing the processing on each pixel (or voxel).

Figure 3:
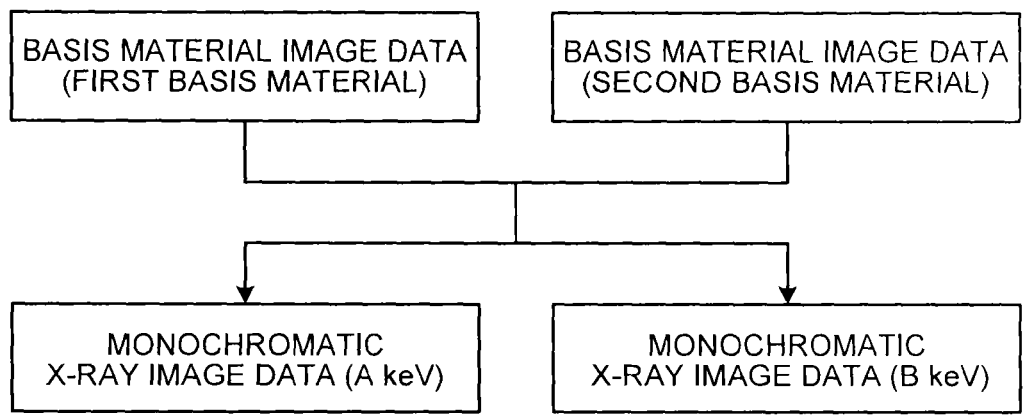
FIG. 3 is a schematic diagram for explaining the reconstructing circuitry according to the present embodiment.

FIG. 3 is a schematic diagram for explaining the reconstructing circuitry according to the present embodiment. For example, the reconstructing circuitry 36a according to the present embodiment generates monochromatic X-ray image data of two kinds of energies (A keV and B keV) from the basis material image data of the first basis material and the basis material image data of the second basis material.

The reconstructing circuitry 36a acquires a linear attenuation coefficient of the pixel "x, y" at "A" by Equation (1), and calculates a CT value of the pixel "i" by substituting this linear attenuation coefficient and the linear attenuation coefficient "$\mu_{water}(A)$" of water at "A" into Equation (2), and thereby generates monochromatic X-ray image data (A keV). Moreover, the reconstructing circuitry 36a acquires the linear attenuation coefficient of the pixel "x, y" of "B" by Equation (1), and calculates a CT value of the pixel "x, y" by substituting this linear attenuation coefficient and the linear attenuation coefficient "$\mu_{water}(B)$" of water at "B" into Equation (2), and thereby generates monochromatic X-ray image data (B keV). An "energy: A" and an "energy: B" may be initially specified in a system, or may be specified by an operator.

Figure 4:
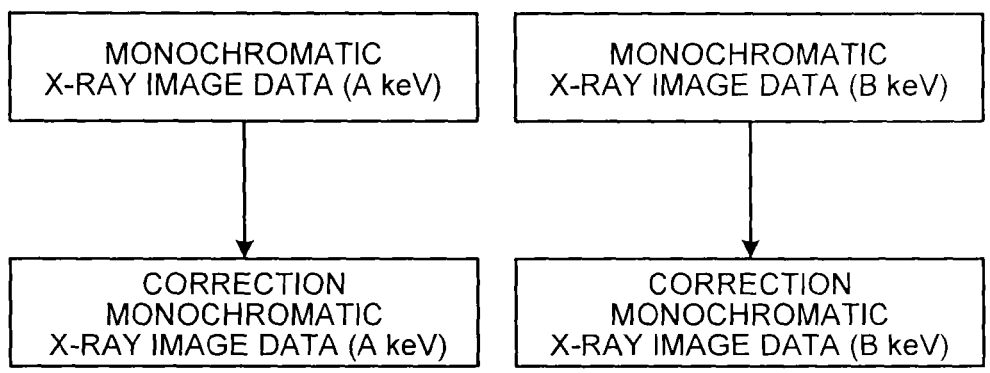
FIG. 4 is a schematic diagram for explaining the image processing circuitry according to the present embodiment.

A pixel value of each pixel in monochromatic X-ray image data is a CT value, and therefore, various kinds of image processing such as a conventional correction processing using CT value information is applicable to the monochromatic X-ray image data. Thus, the image processing circuitry 36b performs an image processing on each of a plurality of pieces of the monochromatic X-ray image data. In the present embodiment, the image processing circuitry 36b performs a correction processing on each of the plurality of pieces of monochromatic X-ray image data as the image processing, to generate a plurality of pieces of corrected monochromatic-X-ray image data. What is explained in the following is also applicable to cases in which an edge enhancement processing, a contrast enhancement processing, and the like are performed as the image processing. Furthermore, what is explained in the following is also applicable to cases in which an edge enhancement processing, a contrast enhancement processing, and the like are performed together with the correction processing as the image processing. FIG. 4 is a schematic diagram for explaining the image processing circuitry according to the present embodiment.

Specifically, the image processing circuitry 36b performs noise reduction using the CT value information, and the like on the monochromatic X-ray image data (A keV) as shown in FIG. 4, to generate corrected monochromatic X-ray image data (A keV). Furthermore, the image processing circuitry 36b performs noise reduction using the CT value information, and the like on the monochromatic X-ray image data (B keV) as shown in FIG. 4, to generate corrected monochromatic X-ray image data (B keV).

Figure 5:
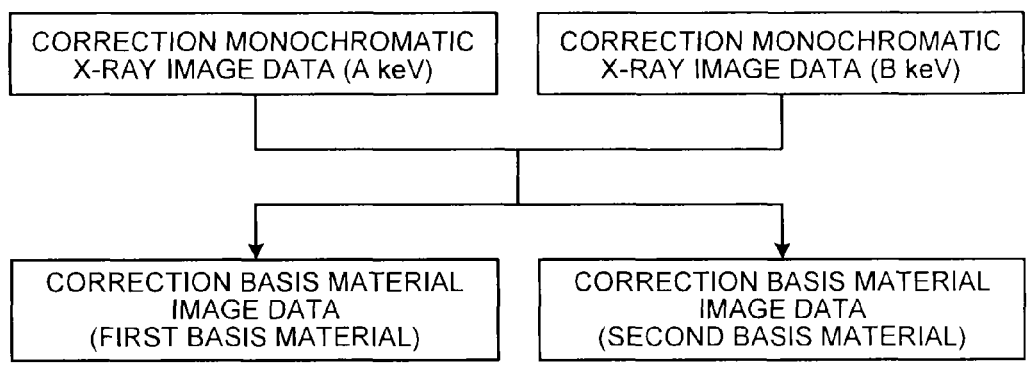
FIG. 5 is a schematic diagram for explaining decomposition circuitry according to the present embodiment.

The decomposition circuitry 36c generates basis material image data of each of the basis materials from the plurality of pieces of monochromatic X-ray image data after the image processing. In the present embodiment, the decomposition circuitry 36c decomposes, for each of the plurality of basis materials, the plurality of pieces of corrected monochromatic X-ray image data, to generate the corrected monochromatic X-ray image data of each of the basis materials. FIG. 5 is a schematic diagram for explaining the decomposition circuitry according to the present embodiment.

Specifically, the decomposition circuitry 36c decomposes the corrected monochromatic X-ray image data (A keV) and the corrected monochromatic X-ray image data (B keV), to generate corrected basis material image data of the first material and the corrected basis material image data of the second basis material as shown in FIG. 5. In the following, the processing performed by the decomposition circuitry 36c is explained using Equation (3) to Equation (6).

A CT value "CT#(A, x, y)" of the pixel "x, y" of the corrected monochromatic X-ray image data (A keV) can be expressed as the following "upper equation of Equation (3)" in which "A" is substituted into "E" in Equation (2). Furthermore, a CT value "CT#(B, x, y)" of the pixel "x, y" of the corrected monochromatic X-ray image data (B keV) can be expressed as the following "lower equation of Equation (3)" in which "A" is substituted into "E" in Equation (2).

$$CT\# (A, x, y) = 1000 \times \frac{\mu(A, x, y) - \mu_{water}(A)}{\mu_{water}(A)} \Biggr\} \quad (3)$$
$$CT\# (B, x, y) = 1000 \times \frac{\mu(B, x, y) - \mu_{water}(B)}{\mu_{water}(B)}$$

"μ(A, x, y)" in the upper equation of Equation (3) expresses a linear attenuation coefficient at the pixel "x, y" of the corrected monochromatic X-ray image data (A keV). Moreover, "μ(B, x, y)" in the lower equation of Equation (3) expresses a linear attenuation coefficient at the pixel "x, y" of the corrected monochromatic-X-ray image data (B keV). The linear attenuation coefficients are ones in which the correction using the CT value information is reflected.

If the upper equation of Equation (3) is transformed into the equation of the linear attenuation coefficient "μ(A, x, y)" in which the correction processing is reflected, the upper equation in following Equation (4) is obtained. Furthermore, if the lower equation of Equation (3) is transformed into the equation of the linear attenuation coefficient "μ(B, x, y)" in which the correction processing is reflected, the lower equation in following Equation (4) is obtained.

$$\mu(A, x, y) = \frac{CT\# (A, x, y) \times \mu_{water}(A)}{1000} + \mu_{water}(A) \Biggr\} \quad (4)$$
$$\mu(B, x, y) = \frac{CT\# (B, x, y) \times \mu_{water}(B)}{1000} + \mu_{water}(B)$$

On the other hand, as described above, the linear attenuation coefficient of the pixel "x, y" at the arbitrary energy "E" is expressed by Equation (1) formed with "$c_1(x, y)$" and "$c_2(x, y)$"; and "$\mu_1(E)$" and "$\mu_2(E)$". Therefore, the linear attenuation coefficient "μ(A, x, y)" in which the correction processing is reflected can be expressed by the following "upper equation in Equation (5)" in which "A" is substituted into "E" in Equation (1). Furthermore, the linear attenuation coefficient "μ(B, x, y)" in which the correction processing is reflected can be expressed by the following "lower equation" in Equation (5) in which "B" is substituted into "E" in Equation (1).

$$\mu(A, x, y) = \mu_1(A) \cdot c_1(x, y) + \mu_2(A) \cdot c_2(x, y) \Biggr\} \quad (5)$$
$$\mu(B, x, y) = \mu_1(B) \cdot c_1(x, y) + \mu_2(B) \cdot c_2(x, y)$$

"$c_1(x, y)$" in the upper equation in Equation (5) is the abundance ratio in which the image processing (correction processing in the present embodiment) of the first basis material at the pixel "x, y" is reflected. Moreover, "$c_2(x, y)$" in the upper equation in Equation (5) is the abundance ratio in which the image processing (correction processing in the present embodiment) of the second basis material at the pixel "x, y" is reflected.

If the upper equation in Equation (5) is transformed into an equation of the abundance ratio "$c_1(x, y)$" in which the correction processing for the first basis material is reflected, the upper equation in following Equation (6) is obtained. Furthermore, if the lower equation in Equation (5) is transformed into an equation of the abundance ratio "$c_2(x, y)$" in which the correction processing for the second basis material is reflected, the lower equation in following Equation (6) is obtained.

$$c_1(x, y) = \frac{\mu(A, x, y) \cdot \mu_2(B) - \mu(B, x, y) \cdot \mu_2(A)}{\mu_1(A) \cdot \mu_2(B) - \mu_1(B) \cdot \mu_2(A)} \Biggr\} \quad (6)$$
$$c_2(x, y) = \frac{\mu(A, x, y) \cdot \mu_1(B) - \mu(B, x, y) \cdot \mu_1(A)}{\mu_2(A) \cdot \mu_1(B) - \mu_2(B) \cdot \mu_1(A)}$$

The linear attenuation coefficient of the first basis material at an arbitrary energy and the linear attenuation coefficient of the second basis material at an arbitrary energy are known. That is, 'the linear attenuation coefficients "$\mu_1(A)$" and "$\mu_1(B)$" of the first basis material at "A" and "B", respectively' and 'the linear attenuation coefficients "$\mu_2(A)$" and "$\mu_2(B)$" of the second basis material at "A" and "B", respectively' can be specified in advance in the decomposition circuitry 36c.

Furthermore, the linear attenuation coefficient "μ(A, x, y)" in which the correction processing is reflected and the linear attenuation coefficient "μ(B, x, y)" in which the correction processing is reflected can be calculated by Equation (4) using the CT values of the corrected monochromatic X-ray image data (A keV) and the corrected monochromatic X-ray image data (B keV).

Accordingly, the decomposition circuitry 36c performs the calculation processing of Equation (4) for each pixel using the corrected monochromatic X-ray image data (A keV) and the corrected monochromatic X-ray image data (B keV). By substituting a result of the calculation processing obtained using Equation (4) into Equation (6), the decomposition circuitry 36c calculates, for each pixel, the abundance ratio of each basis material in which the image processing (correction processing) is reflected. Thus, the decomposition circuitry 36c decomposes two pieces of the corrected monochromatic X-ray image data to generate the corrected basis material image data of the first basis material and the corrected basis material image data of the second basis material.

Figure 6:
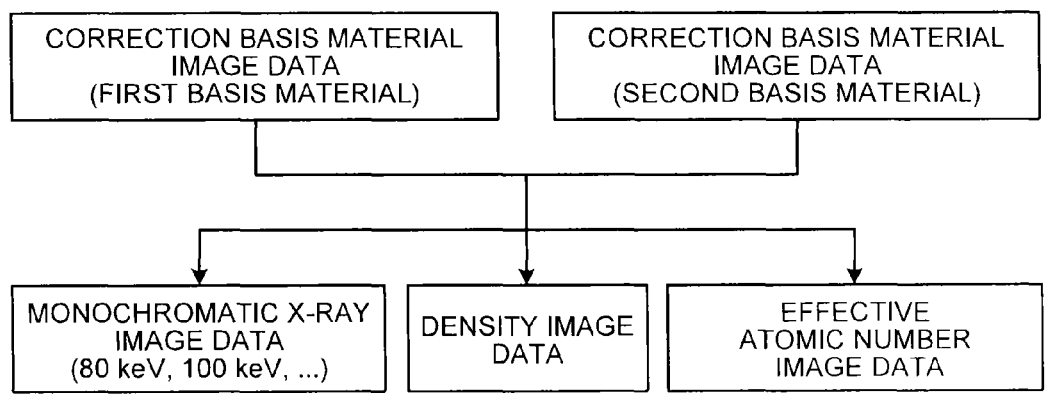
FIG. 6 is a schematic diagram for explaining various kinds of image data that are generated by the reconstructing circuitry according to the present embodiment using corrected basis material image data.

Subsequently, the reconstructing circuitry 36a generates, from the respective basis material image data (corrected basis material image data in the present embodiment) of each of the plurality of basis materials, various kinds of image data, each of the basis material image data being generated by the decomposition circuitry 36c. The processing performed by the reconstructing circuitry 36a subsequent to the processing by the decomposition circuitry 36c is, for example, executed by a setting made by an operator through the input unit 31. FIG. 6 is a schematic diagram for explaining various kinds of image data that are generated by the reconstructing circuitry according to the present embodiment using corrected basis material image data.

Specifically, the reconstructing circuitry 36a generates monochromatic X-ray image data at an arbitrary energy from each of corrected basis material image data of a plurality of basis materials. Because the abundance ratio of each of the basis materials in which the correction processing is reflected has been acquired, the reconstructing circuitry 36a can generate monochromatic X-ray image data at the arbitrary energy using Equation (1). For example, the reconstructing circuitry 36a, as shown in FIG. 6, generates monochromatic X-ray image data of 80 keV and monochromatic X-ray image data of 100 keV from the corrected basis material image data of the first basis material and the corrected basis material image data of the second basis material using Equation (1).

Moreover, the reconstructing circuitry 36a may generate at least one of density image data and effective atomic number image data from the basis material image data (corrected basis material image data in the present embodiment), each of the basis material image data being generated by the decomposition circuitry 36c. Alternatively, the reconstructing circuitry 36a may generate either of monochromatic X-ray image data, density image data, and effective atomic number image data. Alternatively, the reconstructing circuitry 36a may generate at least one of monochromatic X-ray image data, density image data, and effective atomic number image data. For example, the reconstructing circuitry 36a generates density image data and effective atomic number image data from the corrected basis material image data of the first basis material and the corrected basis material image data of the second basis material by performing various kinds of weighting calculations.

The display 32 displays the corrected basis material image data that is generated by the decomposition circuitry 36c, and various kinds of image data that are generated by the reconstructing circuitry 36a using the corrected basis material image data, by the control of the system controlling circuitry 38.

Next, an example of a processing performed by the X-ray CT apparatus according to the present embodiment is explained using FIG. 7. FIG. 7 is a flowchart showing a processing example performed by the X-ray CT apparatus according the present embodiment. In FIG. 7, a case in which the image processing circuitry 36b performs a correction processing as the image processing is explained as an example.

As shown in FIG. 7, the separating circuitry 34b of the X-ray CT apparatus according to the present embodiment determines whether high-energy projection data and low-energy projection data are acquired (step S101). When not yet acquired (step S101: NO), the separating circuitry 34b stays in standby until acquired.

On the other hand, when acquired (step S101: YES), the separating circuitry 34b separates the high-energy projection data and the low-energy projection data into line-integrated data of the first material and line-integrated data of the second material (step S102). The reconstructing circuitry 36a then reconstructs basis material image data of the first basis material and basis material image data of the second basis material (step S103).

Subsequently, the reconstructing circuitry 36a generates two pieces of monochromatic X-ray image data of different energies (step S104), and the image processing circuitry 36b performs a correction processing on each of the two pieces of the monochromatic X-ray image data (step S105).

The decomposition circuitry 36c decomposes the two pieces of the corrected monochromatic X-ray image data to generate corrected basis material image data of the first basis material and corrected basis material image data of the second basis material (step S106). The reconstructing circuitry 36a generates various kinds of image data from the corrected basis material image data of the first basis material and the corrected basis material image data of the second basis material (step S107), and ends the processing.

As described above, in the present embodiment, a plurality of pieces of monochromatic X-ray image data having CT value information are generated from a plurality of pieces of basis material image data, and a correction processing (noise elimination) based on the CT value information is performed. Furthermore, in the present embodiment, corrected basis material image data of respective basis materials in which the correction processing is reflected are generated from the plurality of pieces of the monochromatic X-ray image data after the correction processing. The corrected basis material image data is image data in which the correction processing based on the CT value information is reflected. Moreover, in the present embodiment, also when an image processing based on the CT value information other than the correction processing is performed on the plurality of pieces of monochromatic X-ray image data, basis material image data after image processing of each of the basis materials where the result of the image processing is reflected can be generated. Therefore, in the present embodiment, it is possible to improve the quality of images that are acquired by imaging with a plurality of different tube voltages, in other words, images having no CT value information.

When the number of basis materials is two, for example, the number of unknowns to generate corrected basis material image data is two. Therefore, in the present embodiment, it is preferable that monochromatic X-ray image data be generated with more than two kinds of energy values.

Furthermore, in the present embodiment, for example, from corrected basis material image data of respective basis materials that are generated by performing a correction processing once on a plurality of pieces of monochromatic X-ray image data, monochromatic X-ray image data at an arbitrary energy in which noise is reduced can be generated. Moreover, in the present embodiment, for example, from corrected basis material image data of respective basis materials that are generated by performing a correction processing once, density image data and effective atomic number image data in which noise is reduced can be generated.

The medical image processing method explained in the above embodiment enables to improve the quality of images having no CT value information not only when a correction processing is performed on a plurality of pieces of monochromatic X-ray image data as described above, but also when various kinds of image processing such as an edge enhancement processing are performed. Furthermore, the medical image processing method explained in the above embodiment is applicable also when "multi-energy imaging" with three or more tube voltages is performed. Moreover, the medical image processing method explained in the above embodiment is applicable also when three or more basis materials are specified. However, when N kinds of basis materials are specified, it is preferable that monochromatic X-ray image data be generated with N or more kinds of different energies.

In addition, in the above embodiment, a case in which the X-ray detector 13 is an integral-type detector has been explained. However, the medical image processing method explained in the above embodiment is also applicable to a case in which the X-ray detector 13 is a photon-counting mode detector configured to count individual photons originating from X-rays that have passed through the subject P. When the X-ray detector 13 is a photon-counting mode detector, the separating circuitry 34b performs imaging with one fixed tube voltage and can acquire projection data (line-integrated data) of each basis material from projection data obtained from a photon-counting mode detector. That is, the medical image processing method explained in the above embodiment makes it possible to improve the quality of images having no CT value information even when photon counting CT is performed.

At each incidence of an X-ray photon, the photon-counting mode detector outputs a signal from which an energy value of the X-ray photon can be measured. Suppose the X-ray CT apparatus shown in FIG. 1 is an apparatus that can perform photon counting CT. In this case, at each incidence of an X-ray photon, the detector 13, which is a photon-counting mode detector, outputs an electric signal from which an energy value of the X-ray photon can be measured. The data acquiring circuitry 14 discriminates individual signals that are output from the detector 13, and acquires a position of incidence (position of detection) of the X-ray photon and the energy value of the X-ray photon as counting information for each phase (tube phase) of the X-ray tube 12. The projection data generating circuitry 34a performs a logarithm conversion processing and the like on the counting data that is transmitted from the data acquiring circuitry 14, to generate projection data.

That is, in the projection data acquired by photon counting CT, energy information of an X-ray photon is included. Therefore, the reconstructing circuitry 36a can reconstruct image data from projection data within a predetermined energy range. In other words, the reconstructing circuitry 36a can reconstruct, for example, image data that is equivalent to "monochromatic X-ray image data of A keV" and image data that is equivalent to "monochromatic X-ray image data of B keV" described above. Accordingly, when applied to photon counting CT, the medical image processing method explained in the above embodiment can be performed without performing the "processing of separating projection data into line-integrated data of each of the plurality of basis materials" and the "processing of reconstructing basis material image data from line-integrated data of each of the plurality of basis materials". In this case also, it is possible to improve the quality of images having no CT value information.

Moreover, the medical image processing method explained in the above embodiment may be performed in a medical image processing apparatus that is separately installed from the X-ray CT apparatus. In this case, the medical image processing apparatus receives projection data that is acquired by the X-ray CT apparatus and performs the medical image processing method described above. Alternatively, the medical image processing apparatus receives monochromatic X-ray image data of a plurality of different energies that are generated by the X-ray CT apparatus that performs photon counting CT, and performs the medical image processing method described above.

Each of the structural elements of each of the units/apparatus illustrated in the drawings is of functional concepts, and it is not necessarily required to be configured physically as illustrated. That is, a specific form of decentralization and integration of the respective units/apparatus is not limited to the one illustrated, and it can be configured such that all or a part thereof is functionally or physically decentralized or integrated in an arbitrary unit according to various kinds of loads or usage status. Furthermore, all or arbitrary parts of each of the processing functions performed by the respective units/apparatus can be implemented by a CPU and a program that is analyzed and executed by the CPU, or can be implemented as hardware by a wired logic.

As explained, according to the present embodiment, it is possible to improve the quality of images that are acquired by imaging at a plurality of different tube voltages.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
    image processing circuitry configured to perform a correction process on each of a plurality of pieces of monochromatic X-ray image data of different energies, the plurality of pieces of monochromatic X-ray image data being generated from projection data; and
    decomposition circuitry configured to, after the correction process is performed, decompose, for each of a plurality of basis materials specified in advance, the plurality of pieces of monochromatic X-ray image data on which the correction process has been performed, to generate basis material image data of each of the plurality of basis materials.

2. The X-ray computed tomography apparatus according to claim 1, further comprising:
    separating circuitry configured to separate the projection data into a plurality of pieces of line-integrated data of each of the plurality of basis materials; and
    reconstructing circuitry configured to reconstruct, from each of the plurality of pieces of line-integrated data of each of the plurality of basis materials, basis material image data on which the correction process has not yet been performed, and configured to generate the plurality of pieces of monochromatic X-ray image data using the reconstructed basis material image data of each of the plurality of basis materials.

3. The X-ray computed tomography apparatus according to claim 2, wherein
    the reconstructing circuitry is configured to generate, from the basis material image data of each of the plurality of basis materials, monochromatic x-ray image data of an arbitrary energy, each of the basis material image data being generated by the decomposition circuitry.

4. X-ray computed tomography apparatus according to claim 2, wherein
    the reconstructing circuitry is configured to generate, from the basis material image data of each of the plurality of basis materials, at least one of density image data and effective atomic number image data, each of the basis material image data being generated by the decomposition circuitry.

5. The X-ray computed tomography apparatus according to claim 1, wherein
    the basis material image data is image data in which a pixel value of each pixel indicates an abundance ratio of a basis material that exists in the pixel.

6. The X-ray computed tomography apparatus according to claim 1, wherein number of the pieces of the plurality of monochromatic X-ray image data is equal to number of basis materials specified as the plurality of basis materials.

7. The X-ray computed tomography apparatus according to claim 1, wherein
the projection data is two pieces of projection data collected at two different tube voltages.

8. The X-ray computed tomography apparatus according to claim 1, wherein
the projection data is projection data obtained from a photon-counting mode detector configured to count individual photons originating from X-rays.

9. The X-ray computed tomography apparatus according to claim 1, wherein the plurality of basis materials correspond to bones and water.

10. A medical image processing apparatus, comprising:
image processing circuitry configured to perform a correction process on each of a plurality of pieces of monochromatic X-ray image data of different energies, the plurality of pieces of monochromatic X-ray image data being generated from projection data; and
decomposition circuitry configured to, after the correction process is performed, decompose, for each of a plurality of basis materials specified in advance, the monochromatic X-ray image data on which the correction process has been performed, to generate basis material image data of each of the plurality of basis materials.

* * * * *